(12) United States Patent
Nakamura et al.

(10) Patent No.: US 9,976,960 B2
(45) Date of Patent: May 22, 2018

(54) BASE SEQUENCE ANALYSIS APPARATUS

(71) Applicant: Sony Corporation, Tokyo (JP)

(72) Inventors: Tomohiko Nakamura, Tokyo (JP);
Junji Kajihara, Tokyo (JP)

(73) Assignee: SONY CORPORATION, Tokyo (JP)

(*) Notice: Subject to any disclaimer, the term of this patent is extended or adjusted under 35 U.S.C. 154(b) by 157 days.

(21) Appl. No.: 14/793,176

(22) Filed: Jul. 7, 2015

(65) Prior Publication Data

US 2015/0308959 A1 Oct. 29, 2015

Related U.S. Application Data

(62) Division of application No. 14/047,716, filed on Oct. 7, 2013, now Pat. No. 9,102,978.

(30) Foreign Application Priority Data

Oct. 23, 2012 (JP) ................................ 2012-234227

(51) Int. Cl.
C12Q 1/68 (2018.01)
G01N 21/64 (2006.01)
B01L 7/00 (2006.01)
G01N 21/03 (2006.01)

(52) U.S. Cl.
CPC ............ *G01N 21/6486* (2013.01); *B01L 7/52* (2013.01); *C12Q 1/68* (2013.01); *C12Q 1/6816* (2013.01); *G01N 21/0332* (2013.01); *G01N 21/6408* (2013.01); *G01N 2201/062* (2013.01); *G01N 2201/06113* (2013.01)

(58) Field of Classification Search
None
See application file for complete search history.

(56) References Cited

U.S. PATENT DOCUMENTS

| | | | | |
|---|---|---|---|---|
| 7,629,124 B2* | 12/2009 | Hasson | ................. | C12Q 1/686 435/6.11 |
| 2007/0231799 A1* | 10/2007 | Knight | ............. | B01L 3/502715 435/6.11 |
| 2012/0052563 A1* | 3/2012 | Liang | ..................... | H04N 7/183 435/287.2 |
| 2013/0017544 A1* | 1/2013 | Eckhardt | .......... | B01L 3/502792 435/6.11 |
| 2014/0302501 A1* | 10/2014 | Xu | ...................... | C12Q 1/6883 435/6.11 |

FOREIGN PATENT DOCUMENTS

| | | | | |
|---|---|---|---|---|
| JP | 2012-034617 | | 2/2012 | |
| JP | 2012034617 A | * | 2/2012 | |
| WO | WO 2009156916 A2 | * | 12/2009 | ........... C12Q 1/6832 |
| WO | WO 2014039963 A1 | * | 3/2014 | ........... C12Q 1/6851 |
| WO | WO 2014100725 A1 | * | 6/2014 | ......... G01N 21/6428 |
| WO | WO 2014161975 A1 | * | 10/2014 | ............. C12Q 1/682 |

OTHER PUBLICATIONS

Soon et al. (High Throughput Melting Curve Analysis in Monolithic Silicon-Based Microfluidic Device, 14th International Conference on Miniaturized Systems for Chemistry and Life Sciences, Oct. 3-7, 2010, Groningen, The Netherlands).*
Reed et al. (High-resolution DNA melting analysis for simple and efficient molecular diagnostics, Pharmacogenomics. Jun. 2007;8(6):597-608).*

* cited by examiner

*Primary Examiner* — Aaron A Priest
(74) *Attorney, Agent, or Firm* — Chip Law Group

(57) ABSTRACT

There is provided a base sequence analysis method including: a nucleic acid amplification procedure of obtaining an amplification product by a nucleic acid amplification reaction, a turbidity measurement procedure of measuring turbidity of a reaction solution of the nucleic acid amplification reaction; and a melting curve analysis procedure of performing melting curve analysis of a probe nucleic acid chain and the amplification product at a reaction site of the nucleic acid amplification reaction. This base sequence analysis method makes it possible to consecutively perform a nucleic acid amplification reaction and melting curve analysis at the same reaction site.

9 Claims, 6 Drawing Sheets

BASE SEQUENCE ANALYSIS APPARATUS

CROSS REFERENCES TO RELATED APPLICATIONS

The present application is a divisional of U.S. patent application Ser. No. 14/047,716, filed on Oct. 7, 2013, which claims priority to Japanese Priority Patent Application JP 2012-234227 filed in the Japan Patent Office on Oct. 23, 2012, the entire content of which is hereby incorporated by reference.

BACKGROUND

The present application relates to a base sequence analysis method, a base sequence analysis apparatus, and a base sequence analysis program. More specifically, the present application relates to a base sequence analysis method and the like that includes a turbidity measurement procedure and a melting curve analysis procedure.

The temperature at which a double-stranded nucleic acid chain dissociates (melts) into two single-stranded nucleic acids is called the melting temperature (Tm value). In melting curve analysis, change in a signal detection amount with respect to change in temperature is measured by detecting a signal that changes due to the melting that occurs when a double-stranded nucleic acid chain is gradually heated and melts into two single-stranded nucleic acids. The melting temperature can be determined from a melting curve obtained by plotting the changes in signal detection amount with respect to change in temperature. Since the melting temperature reflects the homology between the two single-stranded nucleic acids, the homology between the two single-stranded nucleic acids can be determined based on the melting temperature. Consequently, melting curve analysis is utilized for analyzing nucleic acids, such as verification of the specificity of a nucleic acid amplification reaction and genotype determination of single nucleotide polymorphisms (SNPs) and the like.

A fluorescent substance is commonly used to detect the melting of a double-stranded nucleic acid chain. For example, by fluorescently labeling a nucleic acid probe capable of forming a double-stranded chain with a target nucleic acid chain, dissociation of the nucleic acid chain can be detected based on the emission or extinguishing of light by the fluorescent label when the target nucleic acid chain and the nucleic acid probe dissociate. Further, change from a double strand to a single strand can be detected using an intercalator that produces fluorescent light by intercalating into a double-stranded nucleic acid.

Fluorescent substances are not limited to melting curve analysis, they are also widely used in detection and quantification of an amplified nucleic acid chain and other such nucleic acid analysis. On the other hand, for amplified nucleic acid chain detection, methods that detect the turbidity of a sample without using a fluorescent substance are also employed. In an extension reaction using a DNA synthesis enzyme, pyrophosphoric acid produced as a byproduct binds with magnesium ions in the reaction solution, thereby forming magnesium pyrophosphate. If the amount of produced magnesium pyrophosphate exceeds the soluble level in the sample, magnesium pyrophosphate precipitates, and the reaction solution turns cloudy. By measuring the level of cloudiness, detection and quantification of an amplified nucleic acid chain can be carried out.

Accordingly, for example, JP-A-2012-34617 discloses a "nucleic acid amplification reaction apparatus including a first light source configured to output light that excites a fluorescent substance, a second light source configured to output light in a wavelength region that matches a wavelength region of fluorescent light produced from the fluorescent substance, and a control unit configured to emit light by switching between the first light source and the second light source, wherein an amount of light produced from turbid matter formed as the amplification reaction progresses and an intensity of fluorescent light produced from the fluorescent substance excited by the light as the amplification reaction progresses can be detected by passing the light from the first light source and the light from the second light source along an optical path where both beams of light are made to overlap by a light guidance member, and irradiating on a reaction area serving as a reaction site of a nucleic acid amplification reaction.

SUMMARY

When performing the above-described melting curve analysis on an amplified nucleic acid chain by a nucleic acid amplification reaction, since the melting curve analysis starts after the nucleic acid has been amplified, the switch from the nucleic acid amplification reaction to melting curve analysis is carried out at a predetermined timing.

According to an embodiment of the present disclosure, there is provided a base sequence analysis method capable of consecutively performing a nucleic acid amplification reaction and melting curve analysis.

According to an embodiment of the present disclosure, there is provided a base sequence analysis method including a nucleic acid amplification procedure of obtaining an amplification product by a nucleic acid amplification reaction, a turbidity measurement procedure of measuring turbidity of a reaction solution of the nucleic acid amplification reaction, and a melting curve analysis procedure of performing melting curve analysis of a probe nucleic acid chain and the amplification product at a reaction site of the nucleic acid amplification reaction.

It is preferable that the melting curve analysis procedure is performed when the turbidity has reached a predetermined value.

Further, it is preferable that the probe nucleic acid chain has a lower melting temperature than a reaction temperature in the nucleic acid amplification reaction.

Further, it is preferable that the probe nucleic acid chain has a lower melting temperature than a melting temperature of a primer used in the nucleic acid amplification reaction and that the nucleic acid amplification reaction is performed in presence of the probe nucleic acid chain.

The probe nucleic acid chain may have a melting temperature that is 5 to 15° C. lower than the melting temperature of the primer.

A plurality of probe nucleic acid chains each having a different base sequence may be used as the probe nucleic acid chain.

The plurality of probe nucleic acid chains each having a different base sequence may each be labeled with a fluorescent substance that emits light having a different wavelength. Among the plurality of probe nucleic acid chains having a different base sequence, one probe nucleic acid chain completely may match a part of a base sequence included in the amplification product.

The nucleic acid amplification reaction may be an isothermal nucleic acid amplification reaction. The isothermal nucleic acid amplification reaction may be performed by a loop-mediated isothermal amplification method.

According to an embodiment of the present disclosure, there is provided a base sequence analysis apparatus including a light source configured to output irradiation light on a reaction site, a detection unit configured to detect light produced from a nucleic acid amplification reaction solution in the reaction site by the irradiation light, a temperature adjustment unit configured to heat or cool the reaction site, and a control unit configured to switch a drive mode of the light source based on a signal input from the detection unit. The control unit is configured to switch the drive mode from a nucleic acid amplification reaction mode to a melting curve analysis mode.

It is preferable that the light source includes a first light source and a second light source and a wavelength of light output from the first light source matches a wavelength region of fluorescent light produced from a fluorescent substance included in the nucleic acid amplification reaction solution irradiated with light from the second light source.

The control unit may be configured to switch the light source outputting the irradiation light to the reaction site from the first light source to the second light source as the switch from the nucleic acid amplification reaction mode to the melting curve analysis mode.

Further, the base sequence analysis apparatus may further include a light guidance member configured to guide the light output from the first light source and the light output from the second light source to an optical path where both beams of light overlap.

Further, the second light source may be one or a plurality of laser light sources and/or LED light sources. The detection unit may detect in a time-division manner fluorescent light produced from the fluorescent substance.

The base sequence analysis apparatus may be provided with a light shielding structure configured to restrict a progression direction of the light output from the light sources and/or the reaction site. The light shielding structure may have a plurality of aperture portions that correspond to a position on a plurality of optical paths between the light sources and the detection unit.

According to an embodiment of the present disclosure, there is provided a base sequence analysis program that causes a computer to execute a nucleic acid amplification procedure of obtaining an amplification product by a nucleic acid amplification reaction, a turbidity measurement procedure of measuring turbidity of a reaction solution of the nucleic acid amplification reaction, and a melting curve analysis procedure of performing melting curve analysis of a probe nucleic acid chain and the amplification product at a reaction site of the nucleic acid amplification reaction.

According to one or more of embodiments of the present disclosure, there is provided a base sequence analysis method and the like capable of consecutively performing a nucleic acid amplification reaction and melting curve analysis at the same reaction site.

Additional features and advantages are described herein, and will be apparent from the following Detailed Description and the figures.

DETAILED DESCRIPTION

Figure 1:
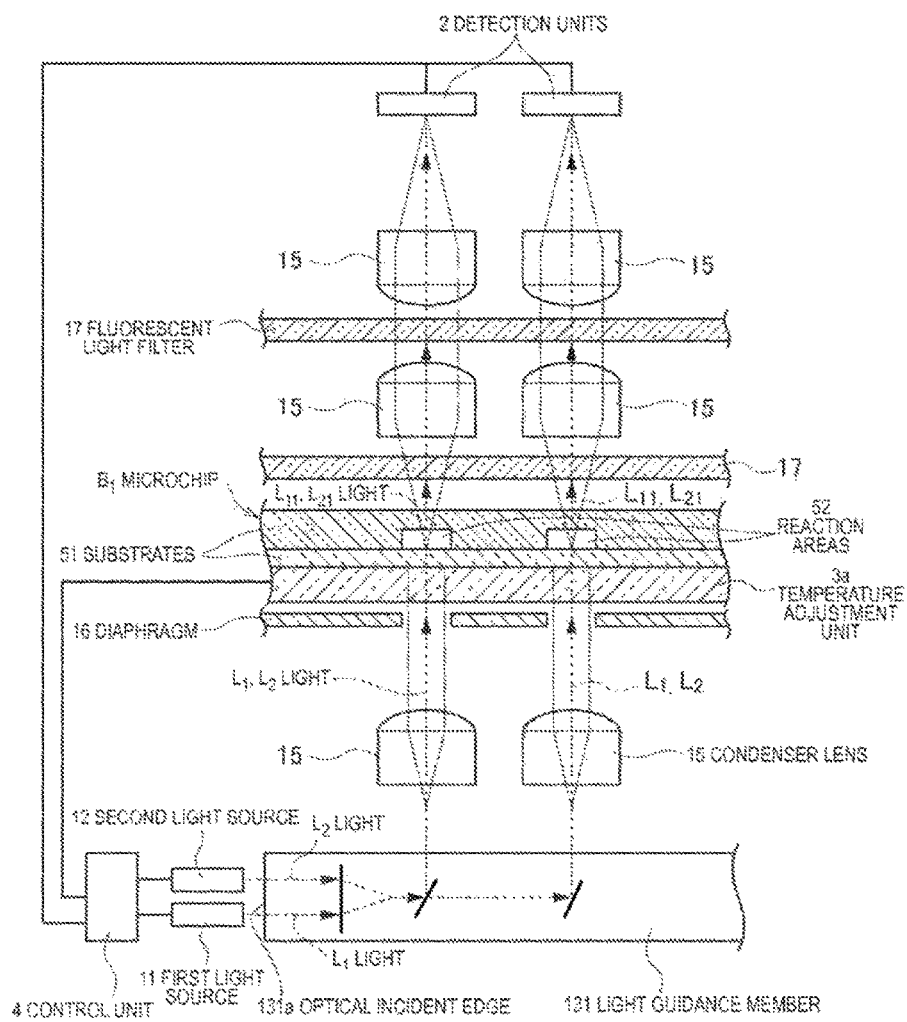
FIG. 1 is a schematic diagram of a base sequence analysis apparatus according to a first embodiment of the present application.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted. The description will be made in the following order.

1. Configuration of the base sequence analysis apparatus according to a first embodiment of the present application
(1) Light source
(2) Detection unit
(3) Temperature adjustment unit
(4) Control unit
(5) Reaction area
2. Operation of the base sequence analysis apparatus according to a first embodiment of the present application
(1) Nucleic acid amplification procedure
(2) Turbidity measurement procedure
(3) Melting curve analysis procedure
3. Configuration of the base sequence analysis apparatus according to a second embodiment of the present application
(1) Excitation filter
(2) Light shielding structure
4. Base sequence analysis method and base sequence analysis program according to an embodiment of the present application 1. Configuration of the Base Sequence Analysis Apparatus According to a First Embodiment of the Present Application FIG. 1 is a schematic diagram of a base sequence analysis apparatus $A_1$ according to a first embodiment of the present application. The base sequence analysis apparatus $A_1$ includes light sources (in FIG. 1, a first light source 11 and a second light source 12) that output irradiation light on reaction areas 52, which are a nucleic acid amplification reaction site, detection units 2 that detect light produced from the nucleic acid amplification reaction occurring in the reaction areas 52 (reaction sites) due to the irradiation light, a temperature adjustment unit 3a that heats or cools the reaction areas 52 (reaction sites), and a control unit 4 that switches the drive mode of the light sources 11 and 12 based on a signal input from the detection units 2. Further, in the base sequence analysis apparatus $A_1$ according to the present embodiment, the first light source 11 and the second light source 12 are included as light sources.

In addition, the base sequence analysis apparatus $A_1$ according to the present embodiment includes a light guidance member 131 that guides the light output from the first light source 11 (first light source) and the light output from the second light source 12 (second light source) to an optical path where these light beams overlap.

Each of the structures in the base sequence analysis apparatus $A_1$ will now be described in order with reference to FIG. 1. It is noted that a nucleic acid amplification reaction solution that is to be analyzed by the base sequence analysis apparatus $A_1$ will be described as being stored in the reaction areas 52 of a microchip $B_1$ that is configured as a separate structure to the base sequence analysis apparatus $A_1$. Further, in FIG. 1, two reaction areas 52 and 52 among a plurality of areas provided in the microchip $B_1$ are illustrated as representatives.

(Light Source)

As illustrated in FIG. 1, the base sequence analysis apparatus $A_1$ includes two types of light source, the first light source 11 and the second light source 12, as light sources that irradiate light on the reaction areas 52.

The first light source 11 outputs light $L_1$ for measuring the turbidity of the nucleic acid amplification reaction solution during the nucleic acid amplification reaction process. It is preferred that the wavelength of the light $L_1$ from the first light source 11 matches the wavelength region of fluorescent light $L_{21}$ produced from a fluorescent substance included in the nucleic acid amplification reaction solution that is irradiated with the light $L_2$ from the second light source 12. The base sequence analysis apparatus $A_1$ includes fluorescent light filters 17 that allows the fluorescent light $L_{21}$ produced from the fluorescent substance excited by the light $L_2$ from the second light source 12 to pass through. Consequently, configuring so that the light $L_1$ output from the first light source 11 has the same wavelength region as the fluorescent light $L_{21}$ coming from the fluorescent substance allows the light $L_1$ to pass through the fluorescent light filters 17, so that the light $L_{11}$ and $L_{21}$ produced in the reaction areas 52 can be detected by the same detection unit 2.

The light $L_1$ from the first light source 11 may be, for example, light that is a mixture of various wavelengths like that is output from a common light source, such as a deuterium lamp, tungsten lamp, xenon lamp, mercury lamp, halogen lamp and the like. The wavelength region that matches the transmission wavelength region of the fluorescent light filters 17 may be, for example, 450 nm or more, and especially 450 to 780 nm.

In melting curve analysis of an amplification product produced by the nucleic acid amplification reaction, the second light source 12 outputs excitation light $L_2$ (denoted as light $L_2$ in FIG. 1) on the fluorescent substance included in the nucleic acid amplification reaction solution. This excitation light $L_2$ has a specific wavelength region that corresponds to the absorption spectrum of the desired fluorescent substance. This wavelength region does not overlap the wavelength region of the fluorescent light $L_{21}$ produced from the fluorescent substance. The excitation light $L_2$ reaches the reaction area 52, and excites the fluorescent substance used in melting curve analysis. Further, the excitation light $L_2$ produced from the fluorescent substance reaches the detection unit 2 via the fluorescent light filters 17.

Examples of the second light source 12 (second light source) include a laser light source, and LED light source, a mercury lamp, a tungsten lamp and the like. These light sources may be used alone or as a combination of a plurality thereof. Especially, a single or a plurality of laser light sources and/or LED light sources is preferred. If the light source is a laser light source, since such a light source has a narrow spectrum width and a high power output, an excitation filter that in the past has been used may be omitted. Further, including a light guide plate in the second light source 12 enables excitation in multiple colors by a plurality of types of laser light source having different wavelengths. This also allows a plurality of excitation light beams having different wavelengths to be output in a time-division manner from the second light source.

In the base sequence analysis apparatus $A_1$ according to the present embodiment, the light guidance member 131 is provided so that the light paths of the light $L_1$ and $L_2$ output from the first light source 11 and the second light source 12, respectively, overlap. Although the light guidance member 131 is an optional structure in the base sequence analysis apparatus according to an embodiment of the present application, using this light guidance member 131 allows the number of condenser lenses 15 and detection units 2 on the light path to be reduced, thereby enabling the size of the overall base sequence analysis apparatus to be reduced.

The light guidance member 131 includes an optical incident edge 131a. The light $L_1$ and $L_2$ output from the first light source 11 or the second light source 12 is incident on the optical incident edge 131a. A member (e.g., a prism, a reflection plate, an uneven portion etc.) that causes the incident light $L_1$ and $L_2$ to head in the direction of the reaction area 52 is provided in the light guidance member 131. Further, in the base sequence analysis apparatus $A_1$, it is preferred to arrange a condenser lens 15 and a diaphragm 16 between the light guidance member 131 and the reaction area 52.

(2) Detection Unit

The detection unit 2 detects the light $L_{11}$ or the fluorescent light $L_{21}$ output from the reaction area 52. The configuration of the detection unit 2 is not especially limited, so long as at least the light $L_{11}$ that includes scattered light from the reaction area 52 irradiated with the light $L_1$ from the first light source 11 or transmitted light that has passed through the reaction area 52, and the fluorescent light $L_{21}$ produced from the reaction area 52 by the excitation light $L_2$ from the second light source 12, can be detected. Examples of the detection unit 2 include an area imaging element such as a CCD or a CMOS element, a PMT (a photomultiplier tube), a photodiode and the like.

Further, it is preferred that the base sequence analysis apparatus $A_1$ includes the fluorescent light filters 17 and condenser lenses 15 between the reaction area 52 and the detection unit 2 on the light path where the light $L_{11}$ including scattered light or transmitted light and the fluorescent light $L_{21}$ reach the detection unit 2. It is preferred that the fluorescent light filters 17 let the fluorescent light $L_{21}$ or the light $L_{11}$ including scattered light or transmitted light from the reaction area 52 to pass through well. The fluorescent light filters 17 may be a multi-band-pass filter, for example. The specific wavelength band may be 450 nm or more, and more specifically, 450 to 750 nm. Further, if the excitation light $L_2$ output from the above-described second light source 12 is output to the reaction area 52 in a time-division manner, it is preferred that the base sequence analysis apparatus $A_1$ has detection units 2 that detect in a time-division manner the fluorescent light $L_{21}$ produced from the fluorescent substance in the reaction area 52.

(3) Temperature Adjustment Unit

The temperature adjustment unit 3a is a structure for heating or cooling so that the reaction areas 52 have a desired temperature. The temperature adjustment unit 3a is not especially limited, as long as it can change the temperature of the reaction areas 52. For example, the temperature adjustment unit 3a may be a transparent conductive film, such as an ITO heater that is permeable to light. It is preferred that the temperature adjustment unit 3a is provided at a position near the reaction areas 52.

(4) Control Unit

The control unit 4 controls the drive of the above-described first light source 11, second light source 12, and temperature adjustment unit 3a. Control of the first light source 11 and the like by the control unit 4 will be described below. The control unit 4 can be configured from a versatile computer that includes a CPU, a memory, a hard disk and the like. An OS, the below-described base sequence analysis program and the like are stored on the hard disk.

(5) Reaction Area

The reaction areas 52 are a reaction site for the below-described nucleic acid amplification reaction and melting curve analysis. The configuration of the reaction areas 52 is not especially limited, as long as the light $L_{11}$ and $L_{21}$ produced from the reaction areas 52 can be measured by the base sequence analysis apparatus $A_1$. The reaction areas 52 may be configured from, for example, a commercially-available plastic tube for a nucleic acid amplification reaction. Alternatively, as illustrated in FIG. 1, the reaction areas 52 may be a grove formed in the microchip $B_1$, for example.

The microchip $B_1$ is laminated from a plurality of substrates 51 and 51. In the base sequence analysis apparatus $A_1$ according to the present embodiment, since the sample housed in the reaction areas 52 is subjected to optical analysis, for the substrates 51 and 51, it is preferred to select a material that is permeable to light, and that has little optical error due to having little intrinsic fluorescence and a small wavelength dispersion. The substrates 51 and 51 can be formed from a material such as glass, and various plastics such as polypropylene, polycarbonate, a cyclo-olefin polymer, polydimethylsiloxane and the like. Further, a part of the reagents used in the nucleic acid amplification reaction and melting curve analysis may be contained in advance in the reaction areas 52.

2. Operation of the Base Sequence Analysis Apparatus According to a First Embodiment of the Present Application Next, operation of the base sequence analysis apparatus $A_1$ according to the first embodiment of the present application will be described with reference to the flowchart illustrated in FIG. 2. As illustrated by this flowchart (FIG. 2), the base sequence analysis method according to an embodiment of the present application includes a nucleic acid amplification procedure (S1), a turbidity measurement procedure (S2), and a melting curve analysis procedure (S3).

(1) Nucleic Acid Amplification Procedure

Figure 2:
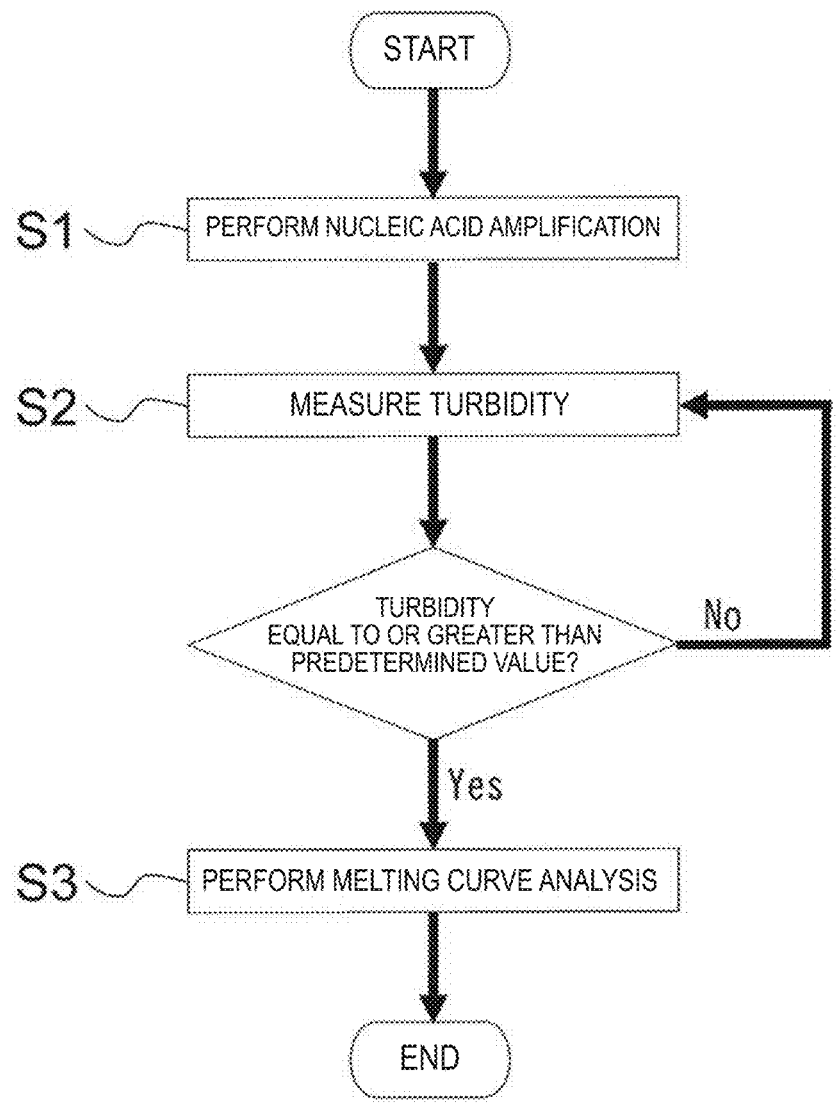
FIG. 2 is a flowchart illustrating a nucleic acid analysis method performed by a base sequence analysis apparatus according to a first embodiment of the present application.

In FIG. 2, reference symbol S1 denotes a nucleic acid amplification procedure for obtaining an amplification product by a nucleic acid amplification reaction. In this procedure S1, a sample (nucleic acid amplification reaction solution) including a nucleic acid chain that is an amplification target is introduced into the reaction areas 52 (refer to FIG. 1), a nucleic acid amplification reaction is carried out, and an amplified nucleic acid chain including a target sequence for melting curve analysis is obtained.

The "nucleic acid amplification reaction" performed using the base sequence analysis apparatus $A_1$ according to the first embodiment of the present application includes a regular PCR (polymerase chain reaction) that employs thermal cycling, as well as various isothermal amplification methods that do not involve thermal cycling. Examples of isothermal amplification methods include methods such as LAMP (loop-mediated isothermal amplification), SMAP (SMart Amplification Process), NASBA (nucleic acid sequence-based amplification), ICAN® (isothermal and chimeric primer-initiated amplification of nucleic acids), TRC (transcription-reverse transcription concerted), SDA (strand displacement amplification), TMA (transcription-mediated amplification), RCA (rolling circle amplification) and the like. In addition, the "nucleic acid amplification reaction" widely includes nucleic acid amplification reactions that are carried out under a varying temperature or a constant temperature, which are directed to the amplification of nucleic acids.

If the nucleic acid amplification reaction involves a temperature cycle or a heating operation, the heating of the sample in the reaction areas 52 can be carried out by the temperature adjustment unit 3a. Further, the base sequence analysis apparatus $A_1$ may be configured so that the heating or cooling performed by the temperature adjustment unit 3a is controlled by the control unit 4.

It is preferred that the nucleic acid amplification reaction performed using the base sequence analysis apparatus $A_1$ is an isothermal nucleic acid amplification reaction that does not involve a temperature cycle. It is especially preferred to carry out the nucleic acid amplification reaction based on a loop-mediated isothermal amplification (LAMP) method. In a LAMP method, since a large quantity of bases are involved in nucleic acid amplification due to there being a large amount of amplification product, the below-described turbidity measurement is easy.

The sample (nucleic acid amplification reaction solution) in the reaction areas 52 includes the nucleic acid chain that is the amplification target in the nucleic acid amplification reaction and the reagents that are used in the nucleic acid amplification reaction. Specifically, these reagents may be an oligonucleotide primer (hereinafter also referred to simply as "primer") that is complementary to at least a part of the base sequence of the nucleic acid chain that is the target of amplification, nucleic acid monomers (dNTPs), enzymes, the components included in the reaction buffer solution and the like. Further, it is preferred that the probe nucleic acid chain that is used in the below-described melting curve analysis is also included as a reagent. In the base sequence analysis method according to an embodiment of the present application, by carrying out the nucleic acid amplification reaction of the nucleic acid amplification procedure S1 in the presence of a probe nucleic acid chain for melting curve analysis, the melting curve analysis can be started immediately after the procedure for obtaining the amplified nucleic acid chain by the nucleic acid amplification reaction.

It is preferred that the melting temperature (Tm) of the probe nucleic acid chain is lower than the reaction temperature of the nucleic acid amplification reaction. More preferably, the melting temperature is lower than the melting temperature of the primer used in the nucleic acid amplification reaction so that the amplification of the amplified nucleic acid chain and the double-stranded nucleic acid is not hindered during the nucleic acid amplification reaction. It is especially preferred that the melting temperature of the probe nucleic acid chain is 5 to 15° C. lower than the melting temperature of the primer. The melting temperature of the probe nucleic acid chain can be actually measured by carrying out the melting curve analysis under the conditions in which the nucleic acid amplification reaction is actually performed. Further, the melting temperature can be calculated by appropriately selecting a known method, such as a nearest neighbor method, a Wallace method, GC % method and the like.

In procedure S1, the control unit 4 of the base sequence analysis apparatus $A_1$ selects "nucleic acid amplification reaction mode" as the drive mode. The "nucleic acid amplification reaction mode" is a mode in which each structure in the base sequence analysis apparatus $A_1$ is controlled in a state that is suited to amplification of the nucleic acid included in the nucleic acid amplification reaction solution that is in the reaction areas 52. Specifically, in an apparatus like the base sequence analysis apparatus $A_1$, which has two types of light source (first light source 11 and second light source 12), the first light source 11 used in the turbidity measurement procedure S2 described next is driven. Further, if the nucleic acid amplification reaction employs a method that involves a temperature cycle, the control unit 4 performs the desired temperature cycle by driving the temperature adjustment unit 3a in "nucleic acid amplification reaction mode".

(2) Turbidity Measurement Procedure

In FIG. 2, reference symbol S2 denotes a turbidity measurement step for measuring the turbidity of the nucleic acid amplification reaction solution. In this procedure, a determination is made whether the nucleic acid has been amplified by measuring the turbidity of the nucleic acid reaction solution in the reaction areas 52 in which the nucleic acid amplification reaction was carried out in the nucleic acid amplification procedure S1.

Examples of the bases produced in the nucleic acid amplification reaction include bases produced from pyrophosphoric acid and a metal ion capable of binding thereto. If the produced amount of these bases is more than the amount that can dissolve in the nucleic acid amplification reaction solution, the bases precipitate and form turbid matter. In the base sequence analysis method according to an embodiment of the present application, the turbid matter that is the target of the turbidity measurement is not especially limited, as long as the turbid matter is produced by the nucleic acid amplification reaction, and can be optically measured.

The turbidity measurement procedure S2 may be started simultaneously with the start of the nucleic acid amplification procedure S1, or may be started after a predetermined duration has elapsed from the start of the nucleic acid amplification procedure S1. If the turbidity measurement is carried out during the amplification process of the nucleic acid chain, like in so-called real time PCR, it is preferred to start the turbidity measurement procedure S2 simultaneously with or very soon after the start of the nucleic acid amplification procedure S1. On the other hand, in the case of determining whether an amplified nucleic acid chain is included in the nucleic acid amplification reaction solution, the turbidity measurement procedure S2 may be started after a predetermined duration has elapsed from the start of the nucleic acid amplification procedure S1.

In the turbidity measurement procedure S2, the control unit 4 outputs the light $L_1$ for turbidity measurement from the first light source 11 at a predetermined timing. The light $L_1$ output from the first light source 11 is irradiated on the reaction areas 52 via the light guidance member 131 and a condenser lens 15. By irradiating with the light $L_1$, the light $L_{11}$ that includes scattered light produced by the turbid matter produced in the nucleic acid amplification reaction process or transmitted light that has passed through the reaction areas 52, is produced at the reaction areas 52. The light $L_{11}$ passes through the fluorescent light filters 17 and is detected by the detection units 2. It is noted that in the turbidity measurement procedure S2, scattered light produced in the reaction areas 52 may be detected, or transmitted light from the reaction areas 52 may be detected, or both of these may be detected. In the base sequence analysis method according to an embodiment of the present application, the method for measuring turbidity is not especially limited.

As illustrated in FIG. 2, for example, the output of the light $L_1$ from the first light source 11 by the control unit 4 may be repeated at predetermined intervals until the turbidity of the nucleic acid amplification reaction solution exceeds a predetermined value for turbidity set in advance. At the point when the turbidity of the nucleic acid amplification reaction solution exceeds this predetermined value, the control unit 4 starts the melting curve analysis procedure S3 that is described next.

Figure 3:
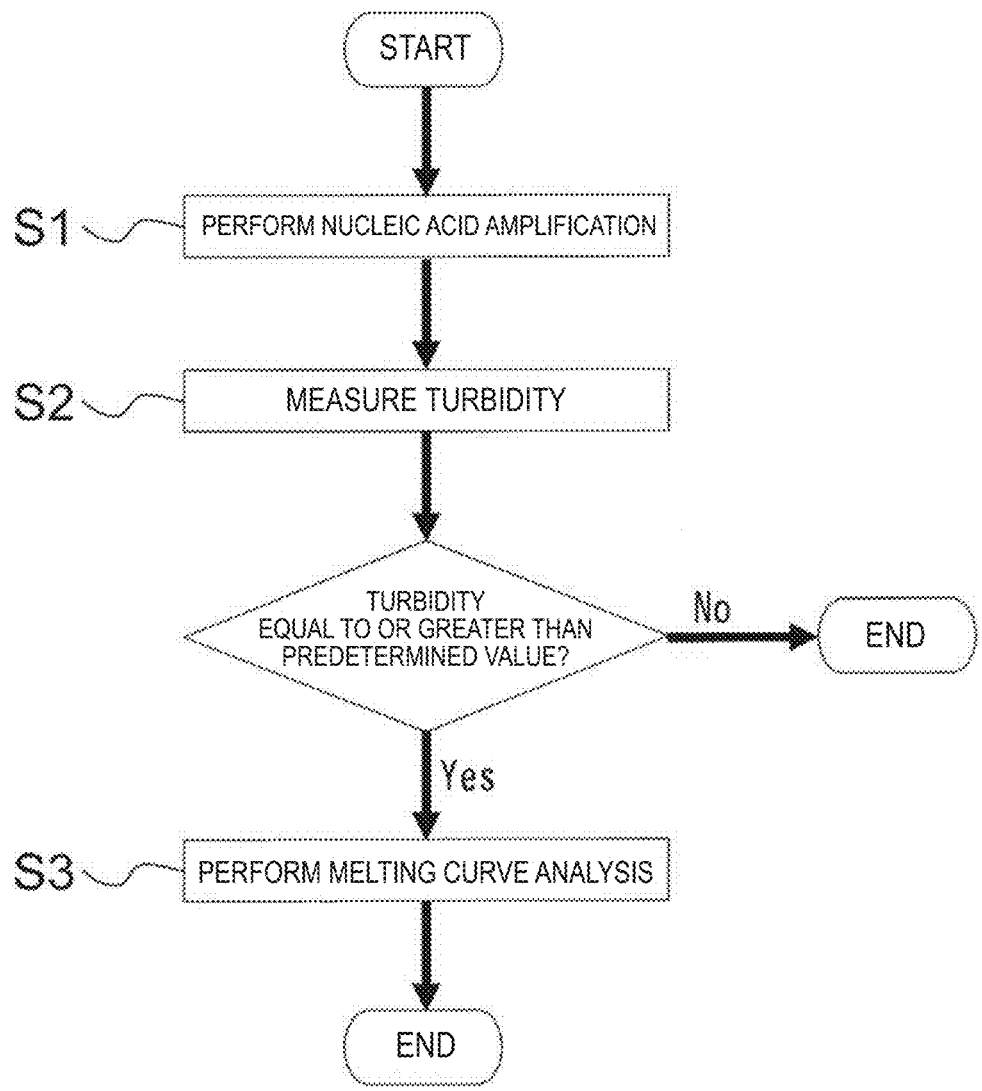
FIG. 3 is a flowchart illustrating a modified example of a nucleic acid analysis method performed by a base sequence analysis apparatus.

On the other hand, as illustrated in FIG. 3, the control unit 4 may also measure the turbidity of the nucleic acid amplification reaction solution by outputting the light $L_1$ from the first light source 11 after a predetermined duration has elapsed from the start of the nucleic acid amplification reaction. When the turbidity of the nucleic acid amplification reaction solution exceeds the predetermined value, the control unit 4 starts the melting curve analysis procedure S3 that is described next. If the turbidity of the nucleic acid amplification reaction solution does not exceed the predetermined value, the control unit 4 determines that the amplified nucleic acid to be used in the melting curve analysis has not been obtained, and thus finishes the base sequence analysis method.

(3) Melting Curve Analysis Procedure

In FIG. 2, reference symbol S3 denotes a melting curve analysis procedure for performing melting curve analysis of the probe nucleic acid chain and the amplification product (amplified nucleic acid chain) at the reaction site of the nucleic acid amplification reaction. It is preferred that this procedure S3 is carried out when the turbidity of the nucleic acid amplification reaction solution has reached the predetermined value. In procedure S3, melting curve analysis of the amplification product is carried out by irradiating excitation light $L_2$ on the reaction areas 52, and measuring the fluorescent light $L_{21}$ produced from the fluorescent substance included in the nucleic acid amplification reaction solution.

The control unit 4 switches the drive mode from nucleic acid amplification reaction mode to melting curve analysis mode, and the starts melting curve analysis procedure S3. The switching of the drive mode by the control unit 4 is preferably carried out at the point when the turbidity of the nucleic acid amplification reaction solution reached the predetermined value based on the light $L_{11}$ produced from the reaction areas 52 (reaction site).

The "melting curve analysis mode" is a mode in which each structure in the base sequence analysis apparatus $A_1$ is controlled in a state that is suited to melting curve analysis of the amplified nucleic acid chain and the probe nucleic acid chain that are included in the nucleic acid amplification reaction solution in the reaction areas 52 based on a signal input by the control unit 4 from the detection units 2. Specifically, in an apparatus like the base sequence analysis apparatus $A_1$, which has two types of light source (first light source 11 and second light source 12), the first light source 11 outputting irradiation light to the reaction areas 52 is switched from the first light source 11 (first light source) to the second light source 12 (2nd light source). It is noted that in procedure S3, the control unit 4 may also control the output timing and power (excitation light wavelength, light amount etc.) and the time-division of the excitation light $L_2$. Further, in procedure S3, in addition to the light sources, the control unit 4 also drives the temperature adjustment unit 3a so that the nucleic acid amplification reaction solution is at a desired temperature.

Examples of the fluorescent substance used in the melting curve analysis procedure S3 include an intercalator that emits fluorescence by binding to a double-stranded nucleic acid and a labeled probe nucleic acid chain that produces fluorescence or loses its fluorescence by forming a double strand. If a probe nucleic acid chain is used, the melting curve can be obtained based on the intensity of the fluorescence that increases or decreases with the melting into a single-stranded nucleic acid. Examples of probe nucleic acid chains that lose their fluorescence by forming a double strand that can be used include the commercially-available QProbe.

In the melting curve analysis procedure S3, a plurality of probe nucleic acid chains having different base sequences may be used. For example, by designing probe nucleic acid chains that have a different amplified nucleic acid chain, base sequences having a plurality of amplified nucleic acid chain moieties can be analyzed by performing the melting curve analysis one time. Further, among the plurality of probes having different base sequences, one probe nucleic acid chain may be designed so as to completely match a portion of the base sequence included in the amplification product. In melting curve analysis that uses a probe nucleic acid chain designed for a portion whose base sequence is unknown, melting curve analysis can also be carried out based on a melting curve obtained from a probe nucleic acid chain that completely matches a portion of the amplified nucleic acid chain.

When using a plurality of probe nucleic acid chains that have different base sequences in one melting curve analysis, it is preferred to label with a fluorescent substance that emits light in various different wavelengths. Examples of the fluorescent substance may include fluorescein and fluorescein isothiocyanate (FITC), which is a kind of derivative of fluorescein, rhodamin and derivatives thereof, and BODIPY dyes.

In the melting curve analysis procedure S3, when using a plurality of types of probe nucleic acid chain labeled with a fluorescent substance, it is preferred to detect the intensity of each fluorescent substance based on the above-described time-division manner.

In the melting curve analysis procedure S3, first, the control unit 4 cools the nucleic acid amplification reaction solution in the reaction areas 52 to a temperature below the melting temperature of the probe nucleic acid chain. When the temperature of the nucleic acid amplification reaction solution has been cooled to below the melting temperature of the probe nucleic acid chain, the probe nucleic acid chain hybridizes into an amplification product and forms a double strand. The cooling is usually carried out from the reaction temperature of the nucleic acid amplification reaction (about 65° C.) to around room temperature to 40° C.

Before cooling the sample, the amplification product (amplified nucleic acid chain) may be heat-denatured. The heat denaturation is performed typically by heating to around 90 to 100° C., and preferably to around 95° C. The double-strand-forming portion of the amplification product is partially dissociated by the heat denaturation. If a probe nucleic acid chain was designed for the double-strand-forming portion of the amplification product, by adding a procedure at the start of procedure S3 of heat-denaturing the amplified nucleic acid chain, the probe nucleic acid chain can be hybridized into the target sequence of the amplified nucleic acid chain.

Next, to obtain the melting curve, the control unit 4 drives the temperature adjustment unit 3a so that the cooled nucleic acid amplification reaction solution is heated. Further, simultaneously with the heating of the nucleic acid amplification reaction solution, the control unit 4 starts the output of the excitation light $L_2$ from the second light source 12.

The amplified nucleic acid chain and the probe nucleic acid chain that are in a hybridized state in the reaction areas 52 melt into a single-stranded nucleic acid due to the increase in temperature of the nucleic acid amplification reaction solution. The fluorescent substance in the nucleic acid amplification reaction solution is irradiated with the excitation light $L_2$ and emits fluorescent light $L_{21}$. The fluorescent light $L_{21}$ passes through the fluorescent light filters 17 and condenser lenses 15, and is detected by the detection units 2. In the melting curve analysis, the temperature usually increases from the post-cooling room temperature (room temperature to 40° C.) to around 90° C., and the changes in the detected amount of fluorescent light with respect to changes in the temperature are measured.

At the point when the nucleic acid amplification reaction solution heated by the temperature adjustment unit 3a reaches the predetermined temperature of around 90° C., the control unit 4 stops the output of the light $L_2$ from the second light source 12, and finishes the melting curve analysis procedure S3. Further, the control unit 4 also stops the heating of the nucleic acid amplification reaction solution by the temperature adjustment unit 3a along with the stopping of the excitation light $L_2$.

In the base sequence analysis apparatus $A_1$ according to an embodiment of the present application, the control unit 4 can continuously perform the nucleic acid amplification reaction and melting curve analysis by, at the point when the turbidity of the nucleic acid amplification reaction solution reaches the predetermined value, switching the drive mode from nucleic acid amplification reaction mode to melting curve analysis mode.

Further, the control unit 4 of the base sequence analysis apparatus $A_1$ can perform the nucleic acid amplification reaction and melting curve analysis in a state in which the sample is held in the same reaction site as the reaction site where the nucleic acid amplification reaction was carried out without adding another procedure, such as confirming the presence of a nucleic acid chain, by switching the light source that is driven after the amplified nucleic acid chain has reached a predetermined concentration.

In addition, in the base sequence analysis method carried out using the base sequence analysis apparatus $A_1$, since the melting temperature of the probe nucleic acid chain is lower than the melting temperature in the nucleic acid amplification reaction, during the nucleic acid amplification reaction, the probe nucleic acid chain is prevented from being hybridized into the amplification target nucleic acid chain. Consequently, even in a state in which the probe nucleic acid chain has been added to the nucleic acid amplification reaction solution, the reagents used in the melting curve analysis can be introduced into the reaction areas before the nucleic acid amplification reaction starts without hindering the nucleic acid amplification reaction, which simplifies the operation for analyzing the base sequence.

Further, in the turbidity measurement procedure for measuring the turbidity of the nucleic acid amplification reaction solution, it is possible carry out the melting curve analysis only on a sample whose probe nucleic acid chain has been confirmed as having been amplified to a level suited to melting curve analysis. Consequently, based on the base sequence analysis method according to an embodiment of the present application, the accuracy of the melting curve analysis of the amplified nucleic acid chain is improved.

Figure 4:
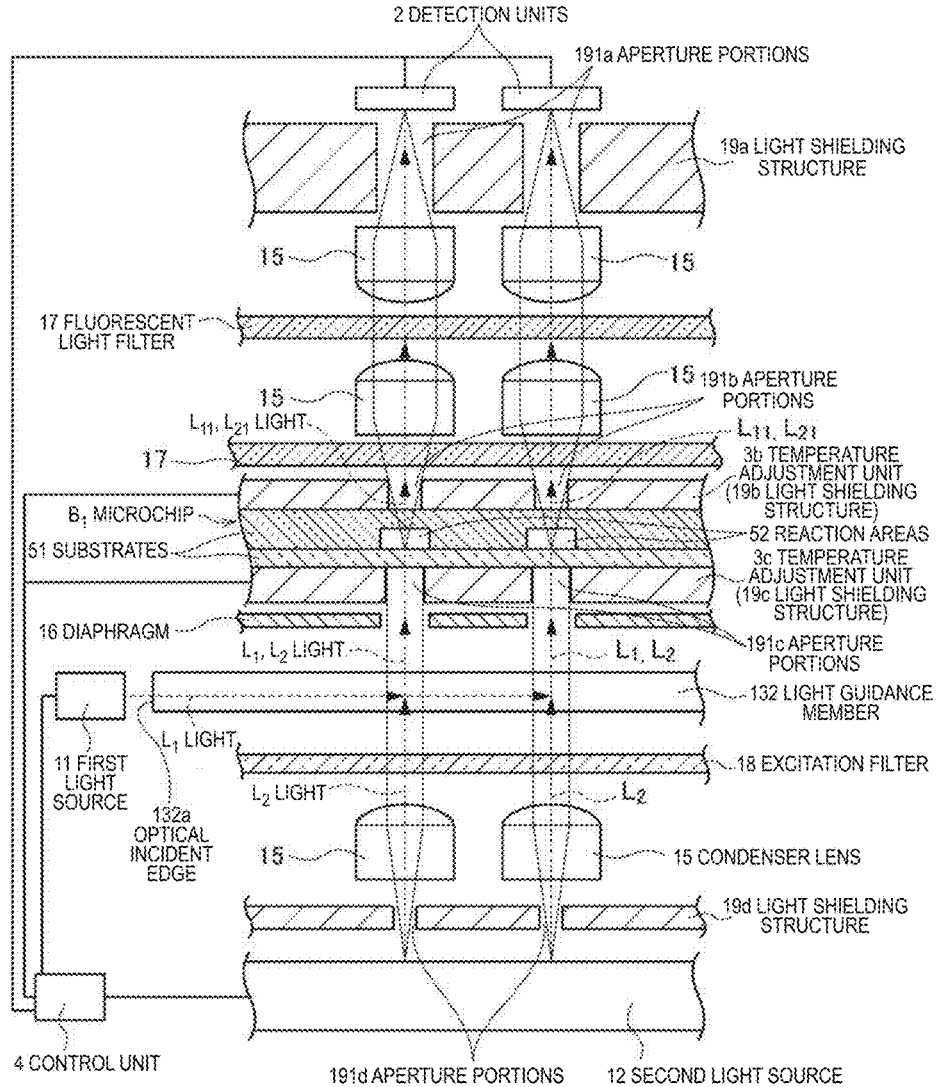
FIG. 4 is a schematic diagram of a base sequence analysis apparatus according to a second embodiment of the present application.

3. Configuration of the Base Sequence Analysis Apparatus According to a Second Embodiment of the Present Application FIG. 4 is a schematic diagram of a base sequence analysis apparatus $A_2$ according to a second embodiment of the present application. The base sequence analysis apparatus $A_2$ has the same configuration as in the first embodiment of the present application, except for an excitation filter 18 and light shielding structures 19a, 19b, 19c, and 19d. The constituent parts that are the same as in first embodiment of the present application are denoted with the same reference numerals, and a description thereof will be omitted here.

(1) Excitation Filter

The base sequence analysis apparatus $A_2$ includes an excitation filter 18 that allows only light of a specific wavelength from the light $L_2$ output from the second light source 12 to pass through. The excitation filter 18 is preferably arranged between the second light source 12 and the reaction areas 52. Further, it is preferred that the excitation filter 18 converts the light $L_2$ output from the second light source 12 into excitation light of a specific wavelength for which the desired fluorescence can be detected.

As illustrated in FIG. 4, since the excitation filter 18 is not provided on the light path of the light $L_1$ output from the first light source 11 used for turbidity measurement, in the base sequence analysis apparatus $A_2$, a light guidance member 132 is provided between the reaction areas 52 and the excitation filter 18. The light guidance member 132 includes an optical incident edge 132a. The light output from the first light source 11 is incident on the optical incident edge 132a. Similar to the first embodiment of the present application, a member (e.g., a prism, a reflection plate, an uneven portion etc.) that causes the incident light to head in the direction of the reaction area 52 is provided in the light guidance member 132. The light $L_2$ output from the second light source 12 and the light $L_1$ output from the first light source 11 pass along a light path where they overlap, and arrive at the reaction areas 52.

It is noted that although two types of light source (the first light source 11 and the second light source 12) are provided in the base sequence analysis apparatus $A_1$ according to the first embodiment of the present application and the base sequence analysis apparatus $A_2$ according to the second embodiment of the present application, the number of light sources provided in the base sequence analysis apparatus according to an embodiment of the present application may be one. In this case, even for light output from one light source, an excitation filter 18 that allows only light in a wavelength region that is suited to turbidity measurement to pass through may be arranged on the optical path to the reaction area at an appropriate timing in the turbidity measurement procedure S2, and an excitation filter 18 that allows only light in the wavelength region that is suited to excitation of the fluorescent substance to pass through may be also arranged on the optical path to the reaction area at an appropriate timing in the melting curve analysis procedure S3, respectively.

(2) Light Shielding Structure

The base sequence analysis apparatus $A_2$ includes light shielding structures 19a and 19b that restrict the progression direction of the light $L_{11}$ and $L_{21}$ output from the reaction areas 52 (reaction site). Further, separate to the purpose of restricting the output direction of the light $L_{11}$ and $L_{21}$ from the reaction areas 52, light shielding structures 19c and 19d are provided to restrict the progression direction of the light $L_1$ and $L_2$ output from the light sources (the first light source 11 and the second light source 12). Namely, in the base sequence analysis apparatus $A_2$, light shielding structures 19a, 19b, 19c, and 19d that suppress the entry of stray light from an adjacent optical system are provided at a plurality of locations adjacent to the optical path between the light sources (the first light source 11 and the second light source 12) and the detection units 2. Since providing the light shielding structures 19a, 19b, 19c, and 19d suppresses stray light, the accuracy of analysis performed using the base sequence analysis apparatus $A_2$ is improved.

In the base sequence analysis apparatus $A_2$ illustrated in FIG. 4, the light shielding structure 19a provided adjacent to the detection units 2 and the light shielding structure 19b provided adjacent to the reaction areas 52 restrict the progression direction of the light $L_{11}$ and $L_{21}$ output from the reaction areas 52. On the other hand, the light shielding structure 19d provided adjacent to the second light source 12 and the light shielding structure 19c provided adjacent to the reaction areas 52 restrict the progression direction of the light $L_1$ and $L_2$ output from the light sources (the first light source 11 and the second light source 12). In the base sequence analysis apparatus $A_2$ according to an embodiment of the present application, the number of light shielding structures 19a, 19b, 19c, and 19d is not especially limited. A light shielding structure may be provided for light that is output from either the light sources (the first light source 11 and the second light source 12) or the reaction areas 52. However, to improve the accuracy of analysis performed using the base sequence analysis apparatus $A_2$, it is preferred that the light shielding structures 19a, 19b, 19c, and 19d are provided at a position that suppresses stray light for each beam of light output from the light sources (the first light source 11 and the second light source 12) and the reaction areas 52.

It is preferred that the light shielding structures 19a, 19b, 19c, and 19d are a plate-like structure having a predetermined thickness. Further, as illustrated in FIG. 4, if the light shielding structures 19b, 19c, and 19d are provided at a position in contact with the substrates 51 and 51 of the microchip $B_1$ forming the reaction areas 52, the light shielding structures may also be a structure that serves as temperature adjustment units 3b and 3c. In addition, the light shielding structures 19a, 19b, 19c, and 19d may also have an aperture portion 191a, 191b, 191c, and 191d. It is preferred to provide a plurality of aperture portions 191a, 191b, 191c, and 191d that correspond to the position of the plurality of optical paths between the light sources (the first light source 11 and the second light source 12) and the detection units 2.

The light shielding structures 19a, 19b, 19c, and 19d can be produced by pattern-forming one or a plurality of aperture portions 191a, 191b, 191c, and 191d on a metal film of stainless steel, copper (Cu), nickel (Ni) or the like by etching using a photolithography method, for example. The aperture portions 191a, 191b, 191c, and 191d are preferably provided opposing a light source (the first light source 11 or the second light source 12) of the light shielding structures 19a, 19b, 19c, and 19d or the reaction areas 52.

In the base sequence analysis apparatus A2 according to the present embodiment, including the excitation filter 18 in the base sequence analysis apparatus A2 enables only light having a wavelength that is suited to excitation of the fluorescent substance to be irradiated on the reaction areas 52 even when using a common light source, such as a deuterium lamp, tungsten lamp, xenon lamp, mercury lamp, halogen lamp and the like, that outputs a mixture of various wavelengths. Further, if the above-described second light source 12 is a laser light source, depending on the fluorescent substance, it may be difficult to obtain a laser having an effective excitation wavelength. However, by using the excitation filter 18, since excitation light having the desired wavelength can be produced, it is possible to select a wide range of fluorescent substances to be used in the melting curve analysis.

Further, in the base sequence analysis apparatus A2, the inclusion of the light shielding structures 19a, 19b, 19c, and 19d enables stray light from surrounding light sources and from the reaction areas to be suppressed. Consequently, even if there is a plurality of adjacent reaction areas 52 like in the microchip B1, highly accurate optical detection can be carried out in the base sequence analysis method without detecting the excitation light from each reaction area 52 by time-division. Moreover, the time taken to detect the light L11 and light L21 output from the plurality of reaction areas 52 can be substantially reduced. In addition, the other configurations and advantageous effects of the present embodiment are the same as the above-described first embodiment of the present application.

4. Base Sequence Analysis Method and Base Sequence Analysis Program According to an Embodiment of the Present Application The base sequence analysis method according to an embodiment of the present application corresponds to the operations executed by the control unit 4 in the above-described base sequence analysis apparatuses A1 and A2. Further, the control unit 4 in the base sequence analysis apparatuses A1 and A2 contains a base sequence analysis program for executing these operations.

The base sequence analysis program according to an embodiment of the present application is stored in a hard disk and read into a memory under the control of the CPU and OS to execute the above-described analysis operation. Further, the base sequence analysis program can be recorded on a computer-readable recording medium. The recording medium is not especially limited, as long as it is a computer-readable recording medium. Specific examples may include disc-shaped recording media, such as a flexible disk and a CD-ROM. In addition, tape-based recording media, such as a magnetic tape, may also be used. Moreover, a part of the processing may be performed using hardware, such as a DSP (digital signal processor), an ASIC (application specific integrated circuit), a PLD (programming logic device), a FPGA (field-programmable gate array) and the like, and high-speed processing carried out in cooperation with the above-described software program.

Additionally, the present application may also be configured as below.

(1) A base sequence analysis method including:
a nucleic acid amplification procedure of obtaining an amplification product by a nucleic acid amplification reaction;
a turbidity measurement procedure of measuring turbidity of a reaction solution of the nucleic acid amplification reaction; and
a melting curve analysis procedure of performing melting curve analysis of a probe nucleic acid chain and the amplification product at a reaction site of the nucleic acid amplification reaction.

(2) The base sequence analysis method according to (1), wherein the melting curve analysis procedure is performed when the turbidity has reached a predetermined value.

(3) The base sequence analysis method according to (1) or (2), wherein the probe nucleic acid chain has a lower melting temperature than a reaction temperature in the nucleic acid amplification reaction, and the nucleic acid amplification reaction is performed in presence of the probe nucleic acid chain.

(4) The base sequence analysis method according to any one of (1) to (3), wherein the probe nucleic acid chain has a lower melting temperature than a melting temperature of a primer used in the nucleic acid amplification reaction.

(5) The base sequence analysis method according to (4), wherein the probe nucleic acid chain has a melting temperature that is 5 to 15° C. lower than the melting temperature of the primer.

(6) The base sequence analysis method according to any one of (1) to (5), wherein a plurality of probe nucleic acid chains each having a different base sequence are used as the probe nucleic acid chain.

(7) The base sequence analysis method according to (6), wherein the plurality of probe nucleic acid chains each having a different base sequence are each labeled with a fluorescent substance that emits light having a different wavelength.

(8) The base sequence analysis method according to (6) or (7), wherein among the plurality of probe nucleic acid chains each having a different base sequence, one probe nucleic acid chain completely matches a part of a base sequence included in the amplification product.

(9) The base sequence analysis method according to any one of (1) to (8), wherein the nucleic acid amplification reaction is an isothermal nucleic acid amplification reaction.

(10) The base sequence analysis method according to (9), wherein the isothermal nucleic acid amplification reaction is performed by a loop-mediated isothermal amplification method.

(11) A base sequence analysis apparatus including:
a light source configured to output irradiation light on a reaction site;
a detection unit configured to detect light produced from a nucleic acid amplification reaction solution in the reaction site by the irradiation light;
a temperature adjustment unit configured to heat or cool the reaction site; and
a control unit configured to switch a drive mode of the light source based on a signal input from the detection unit,
wherein the control unit is configured to switch the drive mode from a nucleic acid amplification reaction mode to a melting curve analysis mode.

(12) The base sequence analysis apparatus according to (11), wherein the light source includes a first light source and a second light source, and
wherein a wavelength of light output from the first light source matches a wavelength region of fluorescent light produced from a fluorescent substance included in the nucleic acid amplification reaction solution irradiated with light from the second light source.

(13) The base sequence analysis apparatus according to (12), wherein the control unit is configured to switch the light source outputting the irradiation light to the reaction site from the first light source to the second light source as the switch from the nucleic acid amplification reaction mode to the melting curve analysis mode.

(14) The base sequence analysis apparatus according to (12) or (13), further including a light guidance member configured to guide the light output from the first light source and the light output from the second light source to an optical path where both beams of light overlap.

(15) The base sequence analysis apparatus according to any one of (12) to (14), wherein the second light source is one or a plurality of laser light sources and/or LED light sources.

(16) The base sequence analysis apparatus according to any one of (12) to (15), wherein the detection unit detects in a time-division manner fluorescent light produced from the fluorescent substance.
(17) The base sequence analysis apparatus according to any one of (11) to (16), wherein the base sequence analysis apparatus is provided with a light shielding structure configured to restrict a progression direction of the light output from the light sources and/or the reaction site.
(18) The base sequence analysis apparatus according to (17), wherein the light shielding structure has a plurality of aperture portions that correspond to a position on a plurality of optical paths between the light sources and the detection unit.

<Experiment 1>

1. Turbidity Measurement of Nucleic Acid Amplification Reaction Solution

The effects of a probe nucleic acid chain on a nucleic acid amplification reaction were investigated by performing an nucleic acid amplification reaction in the presence of the probe nucleic acid chain to be used in melting curve analysis, and measuring the turbidity of the nucleic acid amplification reaction solution.

(Materials and Method)

In the present experiment, a nucleic acid amplification reaction was carried out based on a LAMP method. The genomic DNA of *Bifidobacterium bifidum* was used for the template nucleic acid chain of the amplification target in the nucleic acid amplification reaction. The *Bifidobacterium bifidum* (NBRC No.: 100015) was obtained from the Biological Resource Center (NBRC) of the National Institute of Technology and Evaluation (NITE). Further, the five types of primer shown in Table 1 were used for the amplification of the template nucleic acid chain. Among these, primer FIP has a complementary sequence to 22 bases of a part of the base sequence on the upstream side of the template nucleic acid chain, and a homologous sequence with 20 bases of a part of the base sequence of the template nucleic acid chain on the downstream side. Further, primer BIP has a homologous sequence with 21 bases of a part of the base sequence of the template nucleic acid chain on the upstream side, and a complementary sequence to 20 bases of a part of the base sequence of the template nucleic acid chain on the downstream side. In the present experiment, for convenience, the 22 base portion of the primer FIP on the upstream side will be denoted as primer FIP (F1c), and the 20 base portion of the primer FIP on the downstream side will be denoted as primer FIP (F2). Similarly, the 21 base portion of the primer BIP on the upstream side will be denoted as primer BIP (B1), and the 20 base portion of the primer BIP on the downstream side will be denoted as primer BIP (B2c).

The Tm value of each of the primers was as follows. Primer F3: 64.2° C., primer B3: 61.2° C., primer FIP (F1c): 72.4° C., primer FIP (F2): 68.6° C., primer BIP (B1): 71.1° C., primer BIP (B2c): 66.7° C., and primer LF: 66.5° C. The primer Tm values were calculated using a nearest neighbor method and setting the sodium ion (Na$^+$) concentration to 50 mM, the F3 and B3 primer concentration each to 0.25 μM, the FIP and BIP primer concentration each to 0.2 μM, and the LF primer concentration to 1 μM. For the primer FIP and the primer BIP, Tm values were calculated separately for the upstream side and the downstream side. This is because two states are included in the LAMP method reaction mechanism, a state in which the upstream side of the primer FIP or the primer BIP anneals with the nucleic acid chain, and a state in which the downstream side anneals with the nucleic acid chain.

TABLE 1

| PRIMER | BASE SEQUENCE | SEQ. ID. NO. |
| --- | --- | --- |
| F3 | TGCTCCGGAA TAGCTCCTG | 1 |
| B3 | TGCCTCCCGT AGGAGTCT | 2 |
| FIP | CCAACAAGCT GATAGGACGC GACGCATGTG ATTGTGGGAA AG | 3 |
| BIP | GAGGTAACGG CTCACCAAGG CGCCGTATCT CAGTCCCAAT G | 4 |
| LF | CCATCCCACG CCGATAG | 5 |

The probe nucleic acid chain (refer to Table 2) to be used in melting curve analysis in the below-described Experiment 2 was added to the nucleic acid amplification reaction solution before starting the nucleic acid amplification reaction. In the present experiment, the QProbes shown in Table 2, in which a fluorescent substance was bound to the end of the base sequence, were used as the probe nucleic acid chain. These QProbes were obtained from Nippon Steel & Sumikin Echo-Tech Corporation.

There are three types of probe nucleic acid chain shown in Table 2, Probe 1 having a melting temperature (Tm value) of 74.2° C., Probe 2 having a melting temperature of 53.5° C. and that completely matches a portion of the sequence of the template nucleic acid chain, and Probe 3 having a melting temperature of 54.5° C. and one base that does not match the template nucleic acid chain in the base sequence. The Tm values of each probe nucleic acid chain were calculated using a nearest neighbor method, and setting the sodium ion (Na$^+$) concentration to 50 mM and the probe concentration to 0.2 μM. In the present experiment, one of these three types of probe nucleic acid chain Probes 1 to 3 was added to the nucleic acid amplification reaction solution.

TABLE 2

| PROBE NUCLEIC ACID CHAIN | BASE SEQUENCE | SEQ. ID. NO. |
| --- | --- | --- |
| Probe 1 | CCGGCCTGAG AGGGCGACC | 6 |
| Probe 2 | CTGAGAGGGC GACC | 7 |
| Probe 3 | CTGACAGGGC GACC | 8 |

The above-described template nucleic acid chain, primer, and probe nucleic acid chain were mixed with a LAMP reagent (Eiken Chemical Co., Ltd.). The resultant mixture was dispensed into a nucleic acid amplification reaction vessel to produce a nucleic acid amplification reaction solution (25 μl). Nucleic acid amplification reaction solutions that contained Probe 1 were denoted as test group 1, nucleic acid amplification reaction solutions that contained Probe 2 were denoted as test group 2, and nucleic acid amplification reaction solutions that contained Probe 3 were denoted as test group 3. Table 3 shows the concentrations of the template nucleic acid chain, the primer, and the probe nucleic acid chain in the nucleic acid amplification reaction solutions. The nucleic acid amplification reaction was carried out at 63° C. A Loopamp EXIA (Eiken Chemical Co., Ltd.) was used for the turbidity measurement of the nucleic acid amplification reaction solutions.

TABLE 3

| | CONCENTRATIONS IN NUCLEIC ACID AMPLIFICATION REACTION SOLUTIONS |
|---|---|
| PRIMER F3 | 0.25 μM |
| PRIMER B3 | 0.25 μM |
| PRIMER FIP | 2 μM |
| PRIMER BIP | 2 μM |
| PRIMER LF | 1 μM |
| PROBE NUCLEIC ACID CHAIN | 0.2 μM |
| TEMPLATE NUCLEIC ACID CHAIN | 100 COPIES/μl |

(Results)

Figure 5:
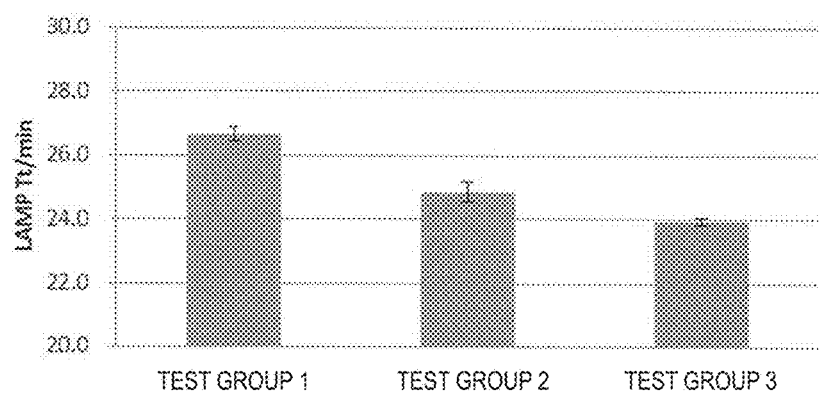
FIG. 5 is a graph illustrating a Tt value based on the turbidity of test groups 1 to 3 measured in Experiment 1.

The results of the present experiment are illustrated in FIG. 5. FIG. 5 illustrates the Tt value (minutes) of test groups 1 to 3 in the nucleic acid amplification reaction. The Tt value (minutes) shown in FIG. 5 is the average value of three samples from each test group. The Tt value is the time taken from the start of the nucleic acid amplification reaction until the rate of increase in the turbidity of the nucleic acid amplification reaction solution exceeded a predetermined threshold. The smaller the Tt value, the greater the efficiency of the nucleic acid amplification reaction.

As illustrated in FIG. 5, based on the results of the turbidity measurement of the nucleic acid amplification reaction solution, it was confirmed that the nucleic acid chain was amplified for all of the tests groups 1 to 3. Further, test groups 2 and 3, which contained a probe nucleic acid chain (Probe 2 and Probe 3) having a melting temperature 9° C. lower than the reaction temperature (63° C.) of the nucleic acid amplification reaction had a smaller Tt value than test group 1, which contained Probe 1 that had a melting temperature close to the reaction temperature.

Based on the results of the present experiment, it was confirmed that a template nucleic acid chain was amplified by the nucleic acid amplification reaction even in the presence of a nucleic acid chain. Further, it was shown that in a nucleic acid amplification reaction carried out in the presence of a nucleic acid chain, the nucleic acid chain is amplified more efficiently if the melting temperature of the probe nucleic acid chain is lower than the reaction temperature of the nucleic acid amplification reaction.

<Experiment 2>

2. Melting Curve Analysis of an Amplified Nucleic Acid Chain and a Probe Nucleic Acid Chain An attempt was made to detect single-base differences in an amplified nucleic acid chain by carrying out melting curve analysis on the amplified nucleic acid chain (amplification product) and the probe nucleic acid chain obtained in Experiment 1.

(Materials and Method)

The amplified nucleic acid chain and the probe nucleic acid chain contained in the nucleic acid amplification reaction solution obtained in the above-described Experiment 1 were used in the melting curve analysis. Namely, the test groups 1 to 3, for which amplification of the nucleic acid had been confirmed in Experiment 1, were used as is in the melting curve analysis of this experiment without replacing the vessel or adding other reagents etc.

The test groups 1 to 3 used in Experiment 1 were cooled to 30° C., and then the melting curve analysis was performed in a temperature range of 30° C. to 90° C. The fluorescence measurement apparatus Chromo 4 (Bio-rad) was used to measure the fluorescence intensity. The fluorescence intensity of each test group was measured every 1° C. The holding time at each temperature was set at 5 seconds.

(Results)

Figure 6:
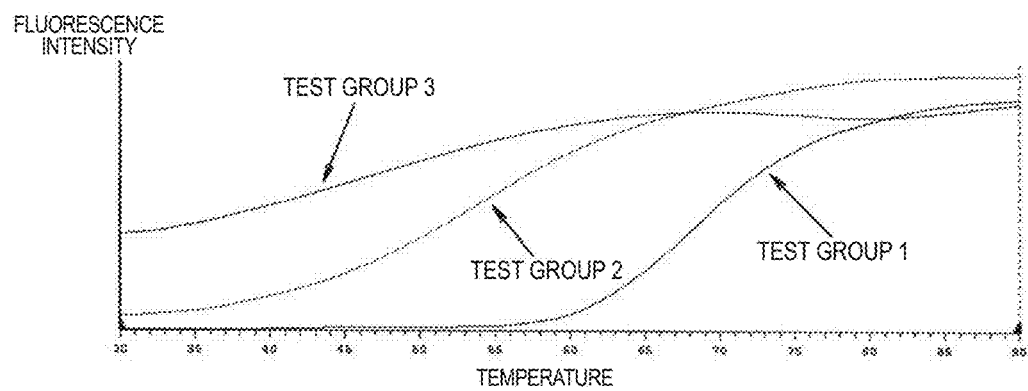
FIG. 6 is a graph illustrating a melting curve of test groups 1 to 3 measured in Experiment 2.

FIG. 6 illustrates the melting curve of test groups 1 to 3 obtained in the present experiment. The ordinate axis in FIG. 6 represents fluorescence intensity based on the probe nucleic acid chain (Probe 1 to 3), which is a QProbe, and the abscissa axis represents temperature.

Since a fluorescently labeled cytosine is present at the end of the QProbes, although the fluorescent substance emits light in a state in which it is not hybridized, if the fluorescent substance is hybridized with the nucleic acid chain, since the fluorescently labeled cytosine pairs with guanine, the fluorescent substance is extinguished due to the effects of guanine. Therefore, the fluorescent substance emits fluorescent light when the probe nucleic acid chain that was hybridized with the nucleic acid chain unlinks from the nucleic acid chain due to the increase in temperature of the nucleic acid amplification reaction solution in melting curve analysis. Further, that fluorescence intensity also increases due to the increase in the probe nucleic acid chain that unlinks from the nucleic acid chain.

Figure 7:
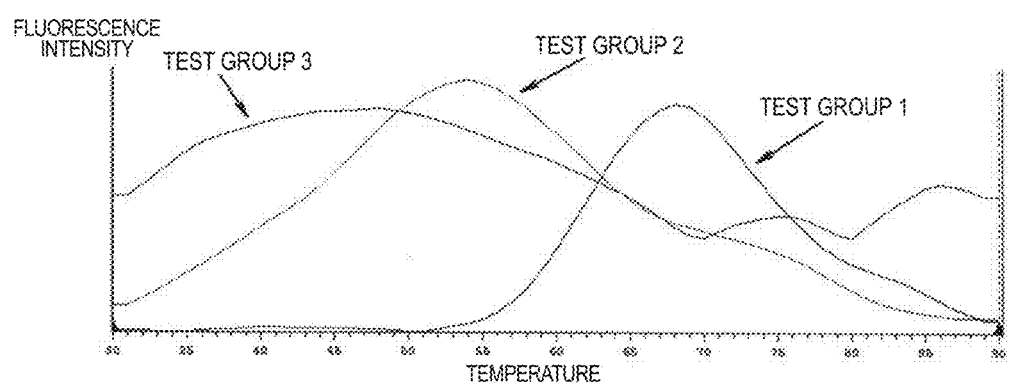
FIG. 7 is a graph illustrating a melting curve of test groups 1 to 3 measured in Experiment 2.

FIG. 7 illustrates the amount of increase in fluorescence intensity per unit time (dI/dT) for the melting curves of test groups 1 to 3. The ordinate axis in FIG. 7 represents fluorescence intensity and the abscissa axis represents temperature. The melting temperature (Tm value) of the nucleic acid chain and the probe nucleic acid chain in each test group estimated from the fluorescence intensity illustrated in FIG. 7 was 68° C. for Probe 1 (test group 1), 54° C. for Probe 2 (test group 2), and 48° C. for Probe 3 (test group 3). For Probe 3, the melting temperature (48° C.) estimated based on the changes in the amount of increase in fluorescence intensity according to melting curve analysis was lower than the melting temperature (54.5° C.) calculated from the base sequence shown in Table 1. This is thought to be due to Probe 3 including in the base sequence a base did not match the amplified nucleic acid chain.

Based on the results of the present experiment, it can be seen that melting curve analysis of an amplified nucleic acid chain and a probe nucleic acid chain can be carried out with a probe nucleic acid chain that is added to a nucleic acid amplification reaction solution before starting a nucleic acid amplification reaction. Further, it can be seen that based on this melting curve analysis, single-base differences between the probe nucleic acid chain and the amplified nucleic acid chain can be detected.

Based on the results of the Experiments 1 and 2, it can be seen that by performing melting curve analysis immediately after measuring the turbidity of a nucleic acid amplification reaction solution, melting curve analysis can be reliably carried out on an amplified nucleic acid chain due to the fact that the melting curve analysis of the amplified nucleic acid chain is started after having confirmed that the nucleic acid chain has been amplified. Further, since the nucleic acid amplification reaction is carried out in the presence of a probe nucleic acid chain, after the nucleic acid amplification reaction, the melting curve analysis can be carried out as is using the same vessel, without adding other reagents to the nucleic acid amplification reaction solution that includes the amplified nucleic acid chain and the probe nucleic acid chain.

SEQUENCE LISTING

<210> 1
<211> 19
<212> DNA
<213> Artificial Sequence

<220>
<223> Synthesized: Primer F3
<400> 1
tgctccggaa tagctcctg 19
<210> 2
<211> 18
<212> DNA
<213> Artificial Sequence
<220>
<223> Synthesized: Primer B3
<400> 2
tgcctcccgt aggagtct 18
<210> 3
<211> 42
<212> DNA
<213> Artificial Sequence
<220>
<223> Synthesized: Primer FIP
<400> 3
ccaacaagct gataggacgc gacgcatgtg attgtgggaa ag 42
<210> 4
<211> 41
<212> DNA
<213> Artificial Sequence
<220>
<223> Synthesized: Primer BIP
<400> 4
gaggtaacgg ctcaccaagg cgccgtatct cagtcccaat g 41
<210> 5
<211> 17
<212> DNA
<213> Artificial Sequence
<220>
<223> Synthesized: Primer LF
<400> 5
ccatcccacg ccgatag 17
<210> 6
<211> 19
<212> DNA
<213> Artificial Sequence
<220>
<223> Synthesized: Probe 1
<400> 6
ccggcctgag agggcgacc 19
<210> 7
<211> 14
<212> DNA
<213> Artificial Sequence
<220>
<223> Synthesized: Probe 2
<400> 7
ctgagagggc gacc 14
<210> 8
<211> 14
<212> DNA
<213> Artificial Sequence
<220>
<223> Synthesized: Probe 3
<400> 8
ctgacagggc gacc 14

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Synthesized: Primer F3

<400> SEQUENCE: 1
tgctccggaa tagctcctg                                                19

<210> SEQ ID NO 2
<211> LENGTH: 18
<212> TYPE: DNA
<213> ORGANISM: Artificial Sequence
<220> FEATURE:
<223> OTHER INFORMATION: Synthesized: Primer B3

<400> SEQUENCE: 2
tgcctcccgt aggagtct                                                 18

<210> SEQ ID NO 3
<211> LENGTH: 42
<212> TYPE: DNA
<213> ORGANISM: Artificial Sequence
<220> FEATURE:
<223> OTHER INFORMATION: Synthesized: Primer FIP

```
<400> SEQUENCE: 3
ccaacaagct gataggacgc gacgcatgtg attgtgggaa ag                              42

<210> SEQ ID NO 4
<211> LENGTH: 41
<212> TYPE: DNA
<213> ORGANISM: Artificial Sequence
<220> FEATURE:
<223> OTHER INFORMATION: Synthesized: Primer BIP

<400> SEQUENCE: 4
gaggtaacgg ctcaccaagg cgccgtatct cagtcccaat g                              41

<210> SEQ ID NO 5
<211> LENGTH: 17
<212> TYPE: DNA
<213> ORGANISM: Artificial Sequence
<220> FEATURE:
<223> OTHER INFORMATION: Synthesized: Primer LF

<400> SEQUENCE: 5
ccatcccacg ccgatag                                                         17

<210> SEQ ID NO 6
<211> LENGTH: 19
<212> TYPE: DNA
<213> ORGANISM: Artificial Sequence
<220> FEATURE:
<223> OTHER INFORMATION: Synthesized: Probe 1

<400> SEQUENCE: 6
ccggcctgag agggcgacc                                                       19

<210> SEQ ID NO 7
<211> LENGTH: 14
<212> TYPE: DNA
<213> ORGANISM: Artificial Sequence
<220> FEATURE:
<223> OTHER INFORMATION: Synthesized: Probe 2

<400> SEQUENCE: 7
ctgagagggc gacc                                                            14

<210> SEQ ID NO 8
<211> LENGTH: 14
<212> TYPE: DNA
<213> ORGANISM: Artificial Sequence
<220> FEATURE:
<223> OTHER INFORMATION: Synthesized: Probe 3

<400> SEQUENCE: 8
ctgacagggc gacc                                                            14
```

The invention claimed is:

1. A base sequence analysis apparatus, comprising:

a first light source and a second light source, wherein the first light source is configured to emit a first light beam to irradiate a reaction site and the second light source is configured to emit a second light beam to irradiate the reaction site;

a detection unit configured to:

detect a third light beam produced from a nucleic acid amplification reaction solution, wherein the third light beam is detected based on the emission of the first light beam and the second light beam, wherein the nucleic acid amplification reaction solution is in the reaction site; and output a signal based on the detection of the third light beam;

a temperature adjustment unit configured to one of heat or cool the reaction site; and a control unit configured to switch a drive mode of the first light source and the second light source between a nucleic acid amplification reaction mode and a melting curve analysis mode, wherein the drive mode is switched based on a turbidity of the nucleic acid amplification reaction solution that is greater than a threshold turbidity value, wherein the turbidity of the nucleic acid amplification reaction solution is measured by at least a portion of the third light beam,
wherein in the nucleic acid amplification reaction mode, the first light source is further configured to emit the first light beam within a first wavelength region,
wherein the first wavelength region of the first light beam corresponds to a second wavelength region of the third light beam, and
wherein in the melting curve analysis mode, the second light source is further configured to emit the second light beam within a third wavelength region different from the second wavelength region.

2. The base sequence analysis apparatus according to claim 1,
wherein the first wavelength region of the first light beam matches a fourth wavelength region of a fluorescent light beam, and
wherein the fluorescent light beam is produced based on a fluorescent substance in the nucleic acid amplification reaction solution that is irradiated with the second light beam emitted from the second light source.

3. The base sequence analysis apparatus according to claim 1, wherein the control unit is further configured to switch the irradiation on the reaction site from the first light source to the second light source based on the switch of the drive mode from the nucleic acid amplification reaction mode to the melting curve analysis mode.

4. The base sequence analysis apparatus according to claim 1, further comprising a light guidance member configured to guide each of the first light beam and the second light beam to a common optical path.

5. The base sequence analysis apparatus according to claim 1, wherein the second light source comprises one of at least one laser light source or at least one LED light source.

6. The base sequence analysis apparatus according to claim 2, wherein the detection unit is further configured to detect in a time-division manner, the fluorescent light beam produced from the fluorescent substance.

7. The base sequence analysis apparatus according to claim 1, further comprising a light shielding structure configured to restrict a direction of propagation of at least one of the first light beam, the second light beam, or the third light beam produced from the reaction site.

8. The base sequence analysis apparatus according to claim 7, wherein the light shielding structure comprises at least one aperture portion that corresponds to a position on an optical path, wherein the optical path is between one of the first light source or the second light source and the detection unit.

9. The base sequence analysis apparatus according to claim 1, wherein the second light source is further configured to emit a plurality of light beams on the reaction site, wherein each light beam of the plurality of light beams is emitted with a different wavelength, and wherein the plurality of light beams include the second light beam.

* * * * *